US009352156B2

(12) United States Patent
Lane et al.

(10) Patent No.: US 9,352,156 B2
(45) Date of Patent: May 31, 2016

(54) AUTOMATIC EVALUATION TECHNIQUE FOR DEEP BRAIN STIMULATION PROGRAMMING

(75) Inventors: Courtney Lane, Ventura, CA (US); Rafael Carbunaru, Valley Village, CA (US); David K. L. Peterson, Valencia, CA (US); Andrew DiGiore, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1215 days.

(21) Appl. No.: 12/976,658

(22) Filed: Dec. 22, 2010

(65) Prior Publication Data

US 2011/0160796 A1    Jun. 30, 2011

Related U.S. Application Data

(60) Provisional application No. 61/290,456, filed on Dec. 28, 2009.

(51) Int. Cl.
*A61N 1/36* (2006.01)
*A61N 1/05* (2006.01)
*A61N 1/372* (2006.01)

(52) U.S. Cl.
CPC ........ *A61N 1/36139* (2013.01); *A61N 1/36082* (2013.01); *A61N 1/0531* (2013.01); *A61N 1/0534* (2013.01); *A61N 1/37282* (2013.01)

(58) Field of Classification Search
USPC ................................ 607/66, 70; 600/544, 595
See application file for complete search history.

(56) References Cited

U.S. PATENT DOCUMENTS

| 5,683,422 | A | 11/1997 | Rise |
| 6,052,624 | A | 4/2000 | Mann |
| 6,516,227 | B1 | 2/2003 | Meadows et al. |
| 6,845,267 | B2 | 1/2005 | Harrison et al. |
| 6,895,280 | B2 | 5/2005 | Meadows et al. |
| 6,909,917 | B2 | 6/2005 | Woods et al. |
| 6,920,359 | B2 | 7/2005 | Meadows et al. |
| 6,950,707 | B2 | 9/2005 | Whitehurst |
| 6,993,384 | B2 | 1/2006 | Bradley et al. |
| 7,539,538 | B2 | 5/2009 | Parramon et al. |
| 2003/0139781 | A1 | 7/2003 | Bradley et al. |
| 2005/0267546 | A1 | 12/2005 | Parramon et al. |
| 2006/0259099 | A1* | 11/2006 | Goetz et al. ...................... 607/66 |
| 2010/0121215 | A1* | 5/2010 | Giftakis et al. ............... 600/544 |

* cited by examiner

*Primary Examiner* — Carl H Layno
*Assistant Examiner* — Jon Eric C Morales
(74) *Attorney, Agent, or Firm* — Faegre Baker Daniels LLP

(57) ABSTRACT

Neurostimulation systems and methods for providing therapy to a patient suffering from a symptom of a disease that latently responds to electrical stimulation therapy are provided. First electrical stimulation energy is conveyed to or from a tissue region of the patient in accordance with a first set of stimulation parameters, thereby affecting the symptom. A predetermined period of time estimated for the symptom to resolve in response to electrical stimulation therapy is allowed to elapse. Second electrical stimulation energy is conveyed to or from the tissue region in accordance with a second set of stimulation parameters different from the first set of stimulation parameters.

22 Claims, 8 Drawing Sheets

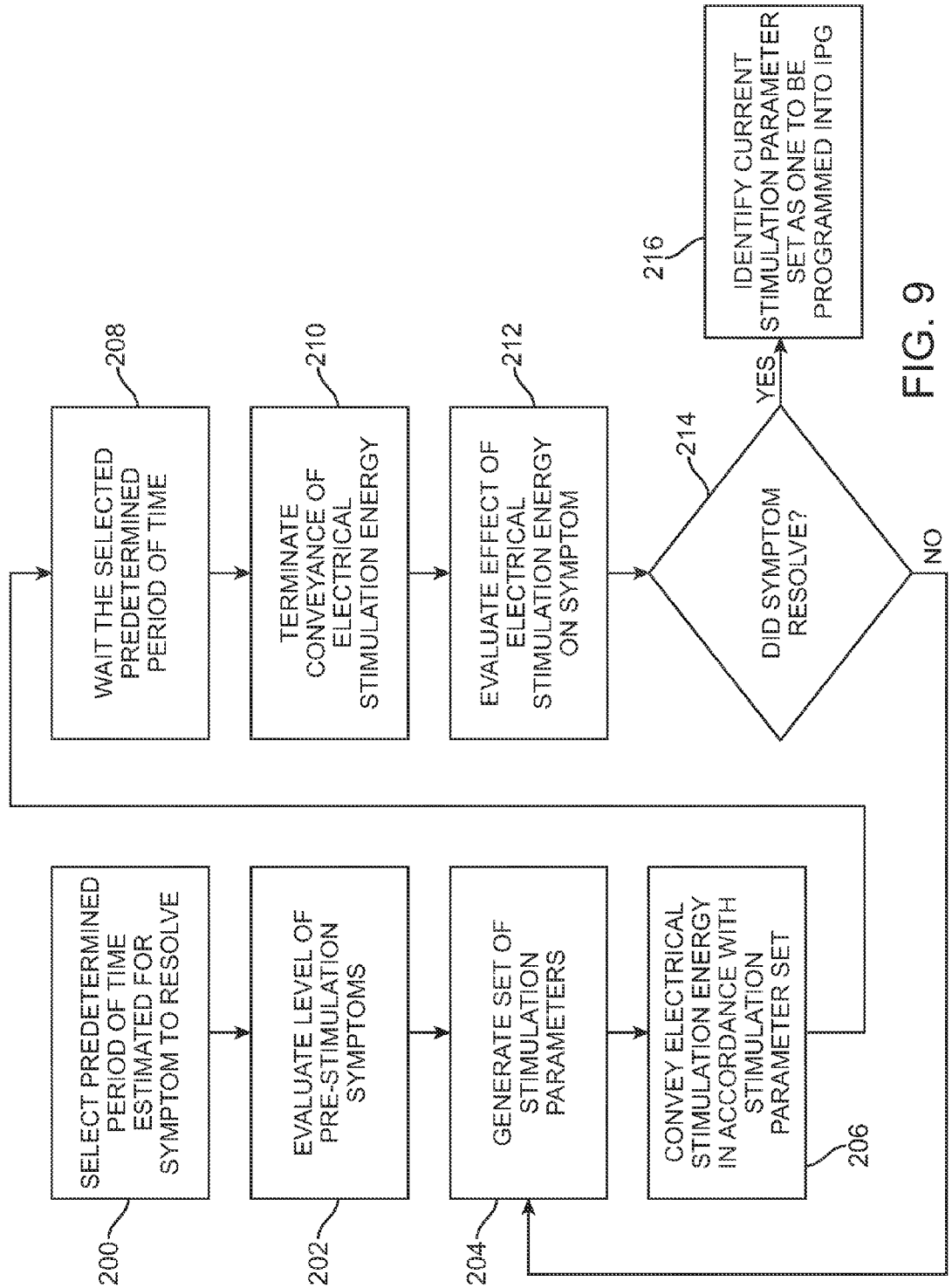

AUTOMATIC EVALUATION TECHNIQUE FOR DEEP BRAIN STIMULATION PROGRAMMING

RELATED APPLICATION

The present application claims the benefit under 35 U.S.C. §119 to U.S. provisional patent application Ser. No. 61/290,456, filed Dec. 28, 2009. The foregoing application is hereby incorporated by reference into the present application in its entirety.

FIELD OF THE INVENTION

The present inventions relate to the treatment of movement disorders, and more particularly, to deep brain stimulation (DBS) systems and methods.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoris and incontinence. Further, in recent investigations, Peripheral Nerve Stimulation (PNS) systems have demonstrated efficacy in the treatment of chronic pain syndromes and incontinence, and a number of additional applications are currently under investigation. More pertinent to the present inventions described herein, Deep Brain Stimulation (DBS) has been applied therapeutically for well over a decade for the treatment of neurological disorders, including Parkinson's Disease, essential tremor, dystonia, and epilepsy, to name but a few. Further details discussing the treatment of diseases using DBS are disclosed in U.S. Pat. Nos. 6,845,267, 6,845,267, and 6,950,707, which are expressly incorporated herein by reference.

Each of these implantable neurostimulation systems typically includes one or more electrode carrying stimulation leads, which are implanted at the desired stimulation site, and a neurostimulator implanted remotely from the stimulation site, but coupled either directly to the stimulation lead(s) or indirectly to the stimulation lead(s) via a lead extension. The neurostimulation system may further comprise a handheld external control device to remotely instruct the neurostimulator to generate electrical stimulation pulses in accordance with selected stimulation parameters. Typically, the stimulation parameters programmed into the neurostimulator can be adjusted by manipulating controls on the external control device to modify the electrical stimulation provided by the neurostimulator system to the patient.

Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of movement disorders), while minimizing the volume of non-target tissue that is stimulated. A typical stimulation parameter set may include the electrodes that are acting as anodes or cathodes, as well as the amplitude, duration, and rate of the stimulation pulses.

Significantly, non-optimal electrode placement and stimulation parameter selections may result in excessive energy consumption due to stimulation that is set at too high an amplitude, too wide a pulse duration, or too fast a frequency; inadequate or marginalized treatment due to stimulation that is set at too low an amplitude, too narrow a pulse duration, or too slow a frequency; or stimulation of neighboring cell populations that may result in undesirable side effects.

The large number of electrodes available, combined with the ability to generate a variety of complex stimulation pulses, presents a huge selection of stimulation parameter sets to the clinician or patient. To facilitate such selection, the clinician generally programs the external control device, and if applicable the neurostimulator, through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback and to subsequently program the external control device with the optimum stimulation parameters.

When electrical leads are implanted within the patient, the computerized programming system may be used to instruct the neurostimulator to apply electrical stimulation to test placement of the leads and/or electrodes, thereby assuring that the leads and/or electrodes are implanted in effective locations within the patient. Once the leads are correctly positioned, a fitting procedure, which may be referred to as a navigation session, may be performed using the computerized programming system to program the external control device, and if applicable the neurostimulator, with a set of stimulation parameters that best addresses the neurological disorder(s).

As physicians and clinicians become more comfortable with implanting neurostimulation systems and time in the operating room decreases, post-implant programming sessions are becoming a larger portion of process. Furthermore, because the body tends to adapt to the specific stimulation parameters currently programmed into a neurostimulation system, follow-up programming procedures are often needed. For example, the brain is dynamic (e.g., due to disease progression, motor re-learning, or other changes), and a program (i.e., a set of stimulation parameters) that is useful for a period of time may not maintain its effectiveness and/or the expectations of the patient may increase. Thus, after the DBS system has been implanted and fitted, the patient may have to schedule another visit to the physician in order to adjust the stimulation parameters of the DBS system if the treatment provided by the implanted DBS system is no longer effective or otherwise is not therapeutically or operationally optimum due to, e.g., disease progression, motor re-learning, or other changes.

Thus, post-implant programming of neurostimulation systems has become a very important part of providing effective therapy to a patient. There are a few issues with current programming methods that need to be addressed.

For example, despite the fact that computerized programming systems have been used to speed up the programming process, performing post-implant programming for an electrical stimulation system still be a relatively time-consuming process. As with many neurostimulation systems, stimulation provided by a DBS system can cause side effects. Current methods to minimize the side effects of neurostimulation include manually changing the stimulation parameters until the side effects are minimized. However, finding the balance between minimal side effects and optimal treatment is difficult to do manually—as there are many factors to evaluate. Furthermore, the physician or clinician that programs the neurostimulators are often trained by experience alone, and lack formal training in the theory of neurostimulation. Therefore, finding the optimal set of stimulation parameter can be hit and miss.

Regardless of the skill of the physician or clinician, these programming sessions can be especially lengthy when programming complicated neurostimulation systems, such as DBS systems, in contrast to other neurostimulation systems, such as SCS systems.

In particular, in some electrical stimulation treatments, the fitting procedure may be effectively directed in response to patient feedback. For example, in SCS for providing pain relief, patients can feel the effects of the stimulation pulses and the change in their pain status, and thus, may provide verbal feedback as to the efficacy of the stimulation, and thus, the proper location of the stimulation leads and/or electrodes and the stimulation parameters to be used in delivering the electrical pulses to the patient on a long-term basis. Unlike with SCS, patients receiving DBS usually cannot feel the effects of stimulation, and the effects of the stimulation may be difficult to observe, are typically subjective, or otherwise may take a long time to become apparent. This makes it difficult to set the stimulation parameters appropriately or otherwise select stimulation parameters that result in optimal treatment for the patient and/or optimal use of the stimulation resources.

Thus, obtaining an optimal program is difficult and sometimes not achieved, resulting in a fitting process that is extremely time consuming and tedious. Exacerbating this problem is the fact that the physician or clinician must manually change the stimulation parameters and evaluate the effects on the patient's symptoms, and therefore, must sit with the patient for the long duration of the programming process, which is a large time commitment.

Besides the problem of requiring a time-consuming programming session that must be manually administered by a physician or clinician, latency issues in the treatment of symptoms often prevent the optimal set of stimulation to be determined. For example, various symptoms of movement disorders, such as Parkinson's disease, take different lengths of time to be suppressed by electrical stimulation. Some symptoms take seconds (e.g., tremor), minutes (e.g., rigidity), or even hours (e.g., bradykinesia) to fade away. However, physicians and clinicians usually program patients at a pace that does not allow symptoms to fully disperse. As a result, they may miss or overlook the best stimulation parameters for treating the symptoms of Parkinson's disease.

While DBS systems have been disclosed that utilize a closed-loop method that involves sensing electrical signals within the brain of the patient and automatically adjusting the electrical stimulation delivered to a target region within the brain of the patient (see, e.g., U.S. Pat. No. 5,683,422), such a system requires the implantation of an additional lead within the brain or inclusion of complex implantable hardware providing updates to the stimulation parameter set. In addition, the electrical signals sensed within the brain are not easily correlatable to the disorder currently experienced by the patient. Furthermore, such a system is not designed to be used in a fitting procedure, including physical adjustment of the leads and programming of the stimulation parameters.

There, thus, remains a need for a DBS system that can be more easily fitted to a patient in order to optimize treatment of a patient suffering from a disease.

SUMMARY OF THE INVENTION

In accordance with one aspect of the present inventions, a neurostimulation system for use with a patient is provided, with the patient suffering from a symptom of a dysfunction that latently responds to electrical stimulation therapy. The neurostimulation system comprises at least one electrical terminal to which at least one electrode can be coupled, and output stimulation circuitry coupled to the electrical terminal(s). The neurostimulation system further comprises memory storing a plurality of predetermined periods of time estimated for a plurality of symptoms to resolve in response to electrical stimulation therapy. In one example, at least one of the predetermined periods of time is equal to or greater than five seconds. In another example, at least one of the predetermined periods of time is equal to or greater than one minute. In still another example, at least one of the predetermined periods of time is equal to or greater than one hour.

The neurostimulation system further comprises control circuitry configured for allowing selection of one of the predetermined periods of time, controlling the output stimulation circuitry to convey first electrical stimulation energy to or from the at least one electrical terminal in accordance with a first set of stimulation parameters, waiting the selected predetermined period of time, and conveying second electrical stimulation energy to or from the tissue region in accordance with a second set of stimulation parameters different from the first set of stimulation parameters. In one embodiment, the control circuitry is configured for terminating conveyance of the first electrical stimulation energy only after waiting the selected predetermined period of time.

The neurostimulation system may optionally comprise processing circuitry configured for evaluating the effect that the first electrical stimulation energy has on the symptom after waiting selected predetermined period of time. In one embodiment, the processing circuitry is further configured for defining the second set of stimulation parameters based on the evaluation. In another embodiment, the processing circuitry is further configured for determining that the symptom did not resolve in response to the first electrical stimulation energy after waiting the selected predetermined period of time, in which case, the second electrical stimulation energy is conveyed in response to the determination that the symptom did not resolve.

In accordance with another aspect of the present inventions, a method of providing therapy to a patient is provided, with the patient suffering from a symptom of a disease (e.g., a neurological disorder, such as Parkinson's disease) that latently responds to electrical stimulation therapy. The method comprises conveying first electrical stimulation energy to or from a tissue region of the patient in accordance with a first set of stimulation parameters, thereby affecting the symptom, and waiting a predetermined period of time estimated for the symptom to resolve in response to electrical stimulation therapy. In one example, the predetermined period of time is equal to or greater than five seconds. In another example, the predetermined period of time is equal to or greater than one minute. In still another example, the predetermined period of time is equal to or greater than one hour. One optional method further comprises selecting one of a plurality of predetermined periods of time estimated for a plurality of symptoms to resolve in response to electrical stimulation therapy, in which case, the selected predetermined period of time is the waited predetermined period of time. In one method, the conveyance of the first electrical stimulation energy is terminated only after waiting the selected predetermined period of time.

The method further comprises conveying second electrical stimulation energy to or from the tissue region in accordance with a second set of stimulation parameters different from the first set of stimulation parameters. The method optionally comprises evaluating the effect that the first electrical stimulation energy has on the symptom after waiting the predetermined period of time. One method further comprises defining the second set of stimulation parameters based on the evaluation. Another method further comprises determining that the symptom did not resolve in response to the first electrical stimulation energy after waiting the predetermined period of time, wherein the second electrical stimulation energy is conveyed in response to the determination that the symptom did not resolve. An optional method further comprises programming the second set of stimulation parameters into the memory of a neurostimulation device.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 9 is a flow diagram illustrating a method of operating the DBS system of FIG. 1 in a specific mode that takes into account latent symptoms of the patient.

DETAILED DESCRIPTION OF THE EMBODIMENTS

At the outset, it is noted that the present invention may be used with an implantable pulse generator (IPG), radio frequency (RF) transmitter, or similar neurostimulator, that may be used as a component of numerous different types of stimulation systems. The description that follows relates to a deep brain stimulation (DBS) system. However, it is to be understood that the while the invention lends itself well to applications in DBS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a spinal cord stimulator, peripheral nerve stimulator, microstimulator, or in any other neural stimulator configured to treat urinary incontinence, sleep apnea, shoulder sublaxation, headache, etc.

Figure 1:
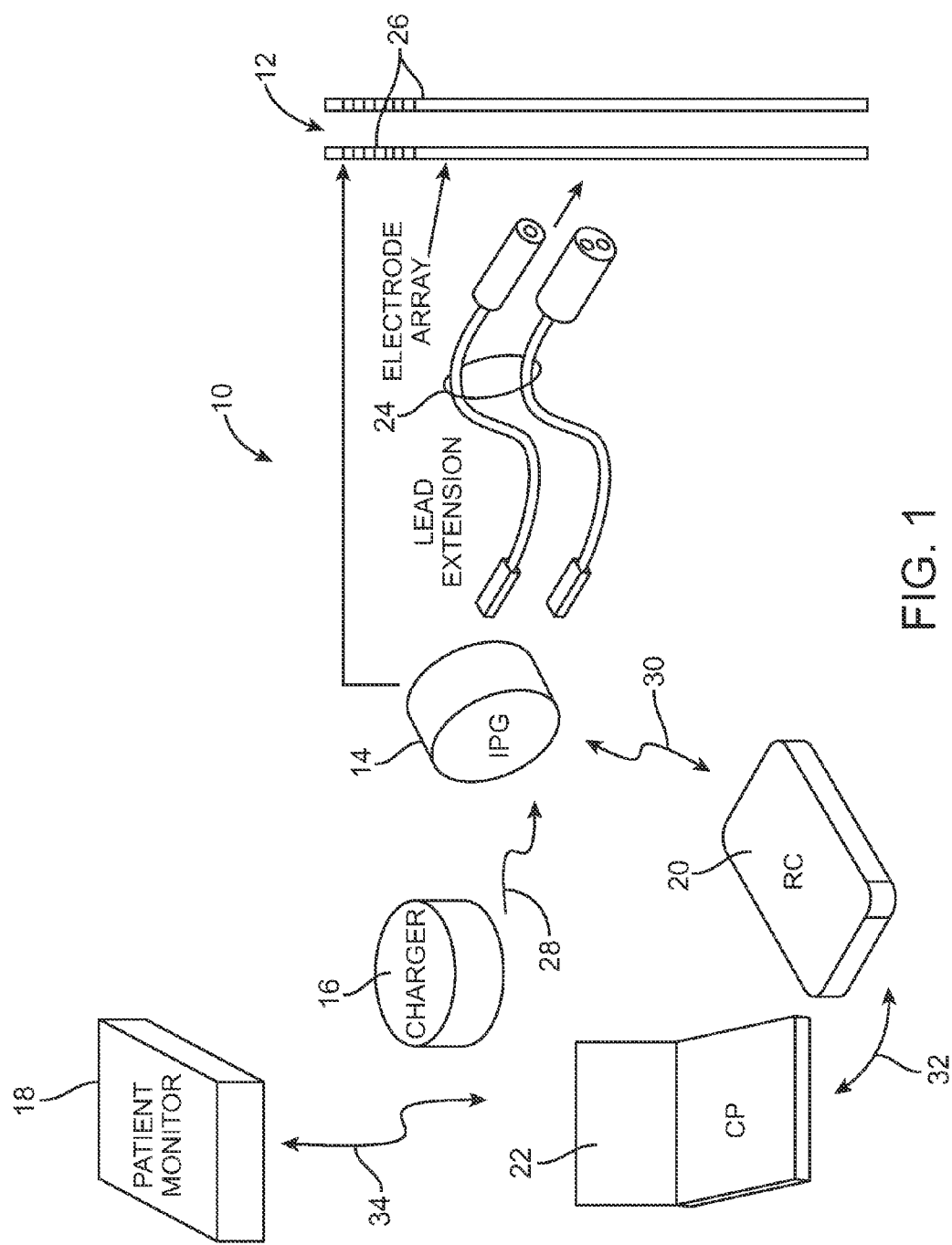
FIG. 1 is a plan view of a Deep Brain Stimulation (DBS) system constructed in accordance with one embodiment of the present inventions.

Turning first to FIG. 1, an exemplary DBS system 10 constructed in accordance with one embodiment of the present inventions generally includes one or more (in this case, two) implantable stimulation leads 12, an implantable pulse generator (IPG) 14 (or alternatively RF receiver-stimulator), an external charger 16, a patient monitor 18, an external remote controller (RC) 20, and a clinician's programmer (CP) 22.

The IPG 14 is physically connected via one or more percutaneous lead extensions 24 to the stimulation leads 12, which carry a plurality of electrodes 26 arranged in an array. In the illustrated embodiment, the electrodes 26 may be arranged in-line along the stimulation leads 12. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The external charger 16 is a portable device used to transcutaneously charge the IPG 14 via an inductive link 28. For purposes of brevity, the details of the external charger 16 will not be described herein. Details of exemplary embodiments of external chargers are disclosed in U.S. Pat. No. 6,895,280, which has been previously incorporated herein by reference.

The patient monitor 18 is used to measure a physiological parameter indicative of the changed status of the symptom or symptoms of the disease from which the patient suffers. Preferably, the physiological parameter that is measured by the patient monitor 18 is a physiological end-function, which for the purposes of this specification, is a physiological function that manifests itself outside of the brain.

The physiological end-function is preferably measured using a non-invasive means (i.e., without having to create an opening within the patient) or otherwise a means that does not require penetration into the patient's brain. Alternatively, the physiological end-function may be invasively measured. The measured physiological end-function may be, e.g., a kinematic action, an electrical muscle impulse, or a speech pattern. The dysfunction may be a motor dysfunction, e.g., a gait dysfunction, posture dysfunction, balance dysfunction, motor control dysfunction (e.g., spasticity, bradykinesia, rigidity), a speech impediment, etc., which may be caused by any one of a variety of diseases, including Parkinson's Disease, essential tremor, dystonia, and epilepsy. The dysfunction may also be a non-motor dysfunction, e.g., psychological, hormonal, etc. The patient monitor 18 may optionally quantify the dysfunction based on the measured physiological end-function; for example, by assigning a numerical value to the dysfunction (e.g., from 1 to 10, with 1 meaning that the dysfunction is non-existent and 10 meaning that the dysfunction is extreme). Additionally, the patient monitor may be a more subjective measure, such as asking the patient if their symptoms (specific or generally) are improved. Many symptoms may be evaluated simultaneously.

The patient monitor 18 may be physically located in a clinical setting where direct physician/assistant control may be exercised under control conditions, or may be located with the patient at a remote setting to allow more limited and/or gradual adjustment of the stimulation parameters. Thus, the patient monitor 18 can be utilized at any time during the treatment continuum to record pre-implant performance, post-implant performance, and follow-up adjustment opportunities. As will be described in further detail below, the measured physiological end-function or quantified dysfunction information can be used to adjust the stimulation parameters in accordance with which the stimulation energy is delivered from the IPG 14.

The RC 20 may be used to telemetrically control the IPG 14 via a bi-directional RF communications link 30 by transmitting stimulation parameters to the IPG 14 or otherwise adjusting the stimulation parameters stored in the IPG 14. Such control allows the IPG 14 to be turned on or off and to be programmed with different stimulation programs after implantation. Once the IPG 14 has been programmed, and its power source has been charged or otherwise replenished, the IPG 14 may function as programmed without the RC 20 being present.

The CP 22 provides clinician-specified stimulation parameters for programming the IPG 14 in the operating room and in follow-up sessions. The CP 22 may perform this function by communicating with the RC 20 via an IR communications link 32 to indirectly program the IPG 14 with the stimulation parameters. The CP 22 may, at the same time, program the RC 20 with the stimulation parameters, so that the RC 20 can subsequently program or otherwise control the IPG 14 using the stimulation parameters programmed into the RC 20. Alternatively, the CP 22 may directly program the stimulation parameters into the IPG 14 via an RF communications link (not shown) without the aid of the RC 20.

The CP 22 may operate in a manual mode or an automated mode. In a manual mode, the CP 22 can be used to program stimulation parameters into the IPG 14 in a conventional manner. In the automated mode, the CP 22 can be used to automatically program stimulation parameters into the IPG 14. In particular, the CP 22 can automatically determine the stimulation parameters to be programmed into the IPG 14 based on the physiological end-function measured by the patient monitor 18. To this end, the CP 22 may receive measured physiological end-function information from the patient monitor 18 via an IR communications link 38. Alternatively, the CP 22 may be coupled to the patient monitor 18 via a cable (not shown). If the patient monitor 18 quantifies the dysfunction based on the measured physiological end-functions, the CP 22 may receive the quantified dysfunction information from the patient monitor 18 via the IR communications link 34, and automatically determine the programmed stimulation parameters based on the quantified dysfunction information. Alternatively, the CP 22, itself, may quantify the dysfunction based on the measured physiological end-function information received from the patient monitor 18. Notably, the CP 22 may automatically determine the stimulation parameters to be programmed into the IPG 14 without user intervention, or may, e.g., provide suggested stimulation parameters, which can be selected by the clinician to ultimately adjust the stimulation parameters programmed into the IPG 14. In any event, the programmed stimulation parameters determined by the CP 22 are intended to improve the status of the dysfunction suffered by the patient.

For example, the CP 22 may control the stimulation energy output by the IPG 14 by adjusting the stimulation parameters in the IPG 14. The patient monitor 18 may measure the physiological end-function of the patient again to determine the effect that the adjustment of the stimulation parameters had on the dysfunction. This process can be repeated until optimized or otherwise effective or improved stimulation parameters are determined, which can then be programmed into the IPG 14. Any delay between the change in the stimulation parameters and the measurement of the physiological end-functions would be controlled and would be affected by the type of dysfunction, physical condition of the patient, the effects of any drugs, etc., allowing the changes in stimulation to take effect before another measurement of physiological end-functions is performed again. Changes due to disease progression, motor re-learning, or other changes that effect the status of the dysfunction can be triggered for re-evaluation of the stimulation parameters programmed into the IPG 14.

The RC 20 can be operated in a manual mode that allows a patient to program stimulation parameters into the IPG 14 in a conventional manner. In alternative embodiments, wherein the patient monitor 18 is located within the patient in a remote setting, the RC 20 may operated in an automated mode in which it automatically determines the stimulation parameters to be programmed into the IPG 14 based on the physiological end-function measured by the patient monitor 18 or the dysfunction quantified by the patient monitor 18, in which case, the RC 20 may be coupled to the patient monitor 18 via an IR communications link (not shown).

The CP 22, or alternatively the RC 20, may determine the improved stimulation parameters based on the measured physiological end-function or quantified dysfunction in any one of a variety of manners to improve the status of the dysfunction. In one embodiment, the stimulation parameters are adjusted using a heuristic approach.

For example, a value of at least one of the stimulation parameters may be incrementally adjusted in one direction (e.g., increasing the pulse amplitude, pulse width, or pulse rate) if the measured physiological end-function indicates an improvement in the status of the dysfunction, and incrementally adjusted in another direction (e.g., decreasing the pulse amplitude, pulse width, or pulse rate) if the measured physiological end-function indicates a degradation in the status of the dysfunction. The value of the stimulation parameters may be incrementally adjusted in the one direction until the measured physiological end-function indicates no further improvement in the status of the dysfunction or until a parameter limit is reached. These stimulation parameters can then be selected as the stimulation parameters to be programmed into the IPG 14.

As another example, different combinations of electrodes may be selected that improve the status of the dysfunction. In one embodiment, the stimulation energy may be gradually steered up or down the leads 12. That is, the stimulation energy may be gradually steered in one direction if the measured physiological end-function indicates an improvement in the status of the dysfunction, and gradually steered in another direction if the measured physiological end-function indicates a degradation in the status of the dysfunction. The improved stimulation parameters, and in this case, the electrode combination, resulting from this process can then be programmed into the IPG 14. Details regarding the steering of stimulation energy amongst electrodes are further disclosed in U.S. Pat. No. 6,052,624, which is expressly incorporated herein by reference.

In another embodiment, the improved stimulation parameters may be determined by correlating the measured physiological end-functions to a desired performance, and with knowledge of past performance and the operational constraints of the IPG 14, determining the stimulation parameters to be programmed into the IPG 14. For instance, normative data for a physiological end-function may be known in the literature and used as a reference for improving the performance of the patient by adjustment of stimulation parameters as described above. Furthermore, past patient physiological performance profiles may be recorded in a database for the patient and compared to for the adjustment methods. An example of this could be gait performance coupled with energy consumption in which speed of gait, stride length, cadence, and joint excursions coupled with the energy utilized (as measured by oxygen uptake) could be used act as a reference for future stimulation parameter adjustments.

As briefly discussed above, the changes in the symptoms of the dysfunction in response to the electrical stimulation are preferably allowed to take full effect before another measurement of physiological end-functions is performed and the stimulation parameters are adjusted. This is especially useful when the dysfunction latently responds to the electrical stimulation, as discussed in the background. For example, when in the automated mode, the CP 22 waits a predetermined period of time between changing the stimulation parameters (e.g., by gradually and incrementally steering the electrical current up or down the leads 12, while waiting the predetermined period of time between changes in the current steering).

The CP 22 may select one of a variety of predetermined period of times (either automatically or in response to user input), each estimated for a specific symptom of the dysfunction to in response to the electrical stimulation energy. For example, if the symptom to be suppressed is tremor, the selected predetermined period of time may be five seconds. If the symptom to be suppressed is rigidity, the selected predetermined period of time may be five minutes. If the symptom to be suppressed is bradykinesia, the selected predetermined period of time may be one hour. In response to receiving the status of the dysfunction from the patient monitor 18, the CP 22 may evaluate the effect that the stimulation energy has on the symptom of the dysfunction after waiting the selected predetermined period of time, and then changing the stimulation parameters if the symptom did not resolve. The CP 22 may additionally evaluate multiple symptoms as well as the power consumption needed to automatically make the trade-off between power consumption and recharge rate and symptom improvement.

Figure 2:
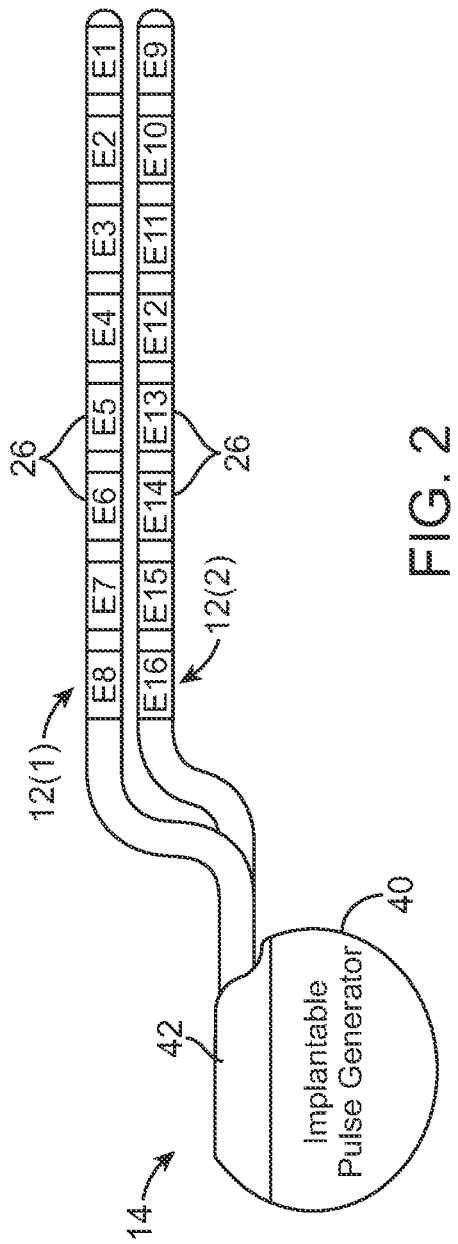
FIG. 2 is a profile view of an implantable pulse generator (IPG) and percutaneous leads used in the DBS system of FIG. 1.

Referring now to FIG. 2, the features of the stimulation leads 12 and the IPG 14 will be briefly described. One stimulation lead 12(1) has eight electrodes 26 (labeled E1-E8), and the other stimulation lead 12(2) has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the stimulation leads 12 mates in a manner that electrically couples the electrodes 26 to the electronics within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

The IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the stimulation on duration X and stimulation off duration Y).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. For example, electrode E3 on the first lead 12(1) may be activated as an anode at the same time that electrode E11 on the second lead 12(1) is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12(1) may be activated as anodes at the same time that electrode E12 on the second lead 12(2) is activated as a cathode.

Figure 3:
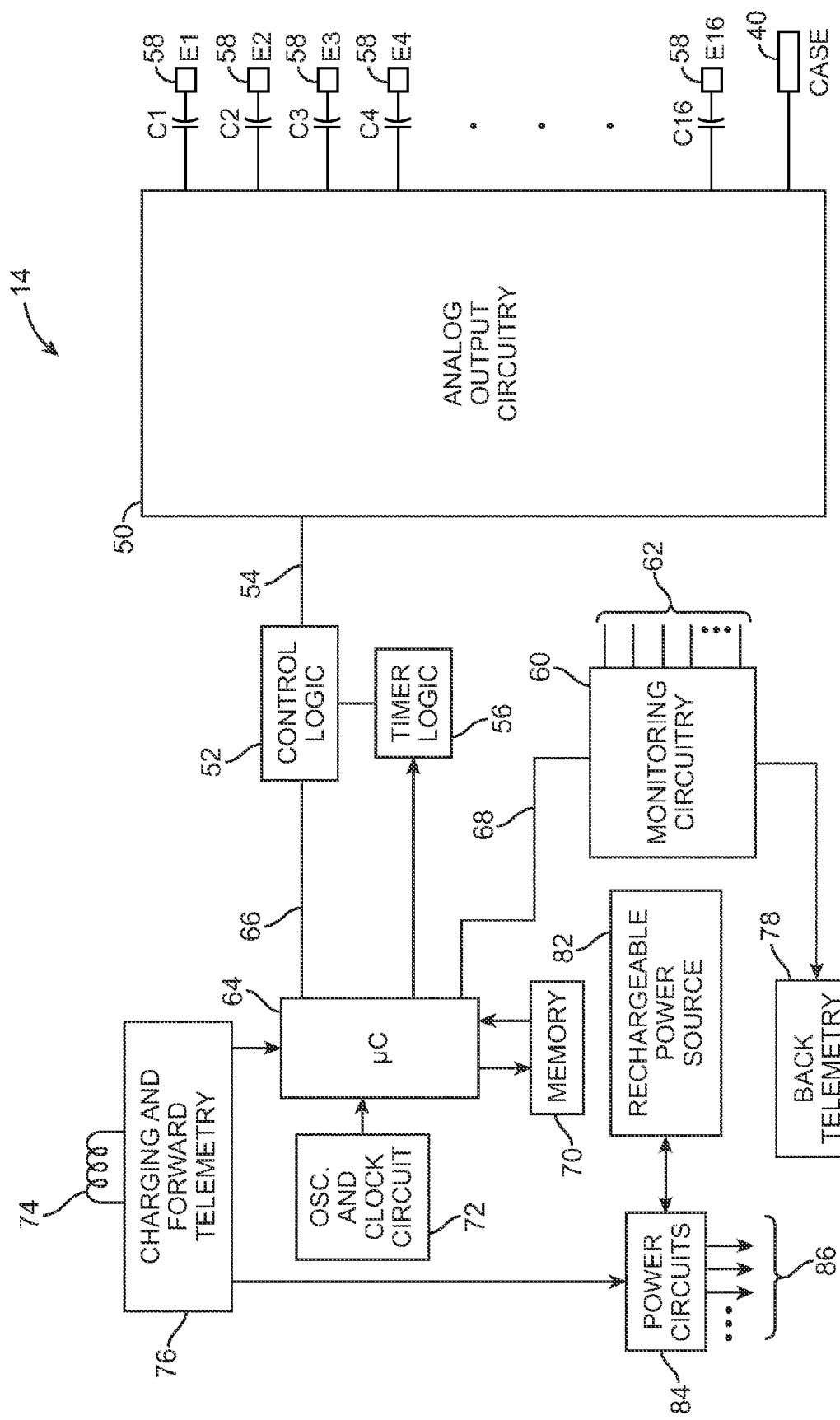
FIG. 3 is a block diagram of the internal components of the IPG of FIG. 2.

Turning next to FIG. 3, the main internal components of the IPG 14 will now be described. The IPG 14 includes stimulation output circuitry 50 configured for generating electrical stimulation energy in accordance with a defined pulsed waveform having a specified pulse amplitude, pulse rate, pulse width, pulse shape, and burst rate under control of control logic 52 over data bus 54. Control of the pulse rate and pulse width of the electrical waveform is facilitated by timer logic circuitry 56, which may have a suitable resolution, e.g., 10 µs. The stimulation energy generated by the stimulation output circuitry 50 is output via capacitors C1-C16 to electrical terminals 58 corresponding to the electrodes 26.

The analog output circuitry 50 may either comprise independently controlled current sources for providing stimulation pulses of a specified and known amperage to or from the electrodes 26, or independently controlled voltage sources for providing stimulation pulses of a specified and known voltage at the electrodes 26. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 14 also comprises monitoring circuitry 60 for monitoring the status of various nodes or other points 62 throughout the IPG 14, e.g., power supply voltages, temperature, battery voltage, and the like. The IPG 14 further comprises processing circuitry in the form of a microcontroller (µC) 64 that controls the control logic 52 over data bus 66, and obtains status data from the monitoring circuitry 60 via data bus 68. The IPG 14 additionally controls the timer logic 56. The IPG 14 further comprises memory 70 and oscillator and clock circuit 72 coupled to the microcontroller 64. The microcontroller 64, in combination with the memory 70 and oscillator and clock circuit 72, thus comprise a microprocessor system that carries out a program function in accordance with a suitable program stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the IPG 14 in accordance with a selected operating program and stimulation parameters. In controlling the operation of the IPG 14, the microcontroller 64 is able to individually generate stimulus pulses at the electrodes 26 using the analog output circuitry 50, in combination with the control logic 52 and timer logic 56, thereby allowing each electrode 26 to be paired or grouped with other electrodes 26, including the monopolar case electrode, to control the polarity, amplitude, rate, pulse width and channel through which the current stimulus pulses are provided.

The IPG 14 further comprises an alternating current (AC) receiving coil 74 for receiving programming data (e.g., the operating program and/or stimulation parameters) from the RC 20 and/or CP 22 in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the IPG 14.

The IPG 14 further comprises back telemetry circuitry 78 and an alternating current (AC) transmission coil 80 for sending informational data sensed through the monitoring circuitry 60 to the RC 20 and/or CP 22. The back telemetry features of the IPG 14 also allow its status to be checked. For example, when the RC 20 and/or CP 22 initiates a programming session with the IPG 14, the capacity of the battery is telemetered, so that the RC 20 and/or CP 22 can calculate the estimated time to recharge. Any changes made to the current stimulus parameters are confirmed through back telemetry, thereby assuring that such changes have been correctly received and implemented within the implant system. Moreover, upon interrogation by the RC 20 and/or CP 22, all programmable settings stored within the IPG 14 may be uploaded to the RC 20 and/or CP 22.

The IPG 14 further comprises a rechargeable power source 82 and power circuits 84 for providing the operating power to the IPG 14. The rechargeable power source 82 may, e.g., comprise a lithium-ion or lithium-ion polymer battery. The rechargeable battery 82 provides an unregulated voltage to the power circuits 84. The power circuits 84, in turn, generate the various voltages 86, some of which are regulated and some of which are not, as needed by the various circuits located within the IPG 14. The rechargeable power source 82 is recharged using rectified AC power (or DC power converted from AC power through other means, e.g., efficient AC-to-DC converter circuits, also known as "inverter circuits") received by the AC receiving coil 74. To recharge the power source 82, an external charger (not shown), which generates the AC magnetic field, is placed against, or otherwise adjacent, to the patient's skin over the implanted IPG 14. The AC magnetic field emitted by the external charger induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications (e.g., programming and control data) and charging energy from the external device, it should be appreciated that the AC receiving coil 74 can be arranged as a dedicated charging coil, while another coil, such as coil 80, can be used for bi-directional telemetry.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the ONS system 10 may alternatively utilize an implantable receiver-stimulator (not shown) connected to leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Referring back to FIG. 1, the patient monitor 18 may take the form of any one of a variety of monitoring devices, several of which are commercially available. The patient monitor 18 may include a peripheral device that measures the physiological end-function of the patient, and a processor, such as a computer, that quantifies the dysfunction of the patient based on the measured physiological end-function. The processor may be separate from the CP 22 (or RC 20), or a portion or the entirety of the processor may be incorporated into the CP 22 (or RC 20).

For example, the patient monitor 18 may be a quantitative motor assessment system that objectively quantifies dysfunctions that involve muscle spasticity (tremor) or muscle limitations (e.g., bradykinesia or rigidity). Exemplary quantitative motor assessment systems designed specifically for patients suffering from Parkinson's Disease are marketed by CleveMed under the trademarks ParkinSense™ and Kinesia™. The ParkinSense™ and Kinesia™ systems are portable, wireless devices that can be attached to the patient using a ring sensor that is placed on a finger of the patient to perform physiological measurements and a wrist module that is electrically coupled to the wrist module via a cable and provides battery power, memory, and real-time transmission. The ring sensor is capable of performing three-dimensional motion detection (using three gyroscopes to obtain orthogonal angular rates, and three accelerometers to obtain orthogonal accelerations). Additional electrodes electrically coupled to the wrist module may be attached to the patient's skin to detect muscle activity (electromyograms). The resulting physiological data is wirelessly transmitted (using Bluetooth radio communication) from the wrist module to a computer, which quantifies the movement disorder based on the data. The computer has a software interface that provides a database to manage and review recorded data files, and clinical videos to guide the patient or clinician through a motor exam based on the Unified Parkinson's Disease Rating Scale, which results in an objective score.

As another example, the patient monitor 18 may be an isokinetic dynamometer that objectively quantifies dysfunctions that involve neuromuscular torque and power and resulting limb movement. An exemplary isokinetic dynamometer specifically designed for performing neuromuscular testing is marketed by Biodex under the trademark Biodex System 3™. The Biodex System 3™ includes a positioning chair in which the patient can be positioned to perform a variety of physical exercises involving movement of the patient's limbs, and a computer system for controlling and implementing the physical exercises, and quantitatively measuring the patient's neuromuscular ability.

As still another example, the patient monitor 18 may be a balance testing device that objectively quantifies dysfunctions that involve balance. An exemplary balance test device specifically designed for performing balance testing is marketed by Biodex under the trademark Balance System SD™. The Balance System SD™ includes a base on which a patient stands and a computer system with a visual biofeedback display that guides the patient through a variety of balancing tests. The base can be manipulated by the computer system to perform the tests in either a static (base remains stable) or dynamic format (base moves). The computer system displays a variety of biofeedback prompts for performing balancing tests, and quantifies the patient's ability to balance based on the performance of these balancing tests.

As still another example, the patient monitor 18 may be a motion tracking system that objectively quantifies dysfunctions that involve any number of aspects, including posture, balance, motor control, and gait. An exemplary motion tracking system is marketed by Vicon under the trademark Peak Motus™. The Peak Motus™ motion tracking system includes a number of high speed video cameras mounted around a room, a number of reflective markers mounted to various locations on the patients body, and a computer for tracking the motion of the patient's limbs, including joint flexion/extension, based on the detected images of the reflective markers as the patient moves about. Based on the tracked motion, the computer can quantify the posture, balance, motor control, and gait of the patient.

While non-invasive means for measuring physiological end-functions have been described herein, invasive means for measuring physiological end-functions may be used. For example, a goniometer could be implanted within the limbs of a patient to measure joint flexion/extension of the limb. Use of an invasive means, such as a goniometer, is advantageous in that it will allow for continuous measurements (or at least more repeatedly) of the physiological end-functions. Alternatively, the electrodes implanted in the brain could be used to measure local-field potentials to provide information for programming while not in use.

Figure 4:
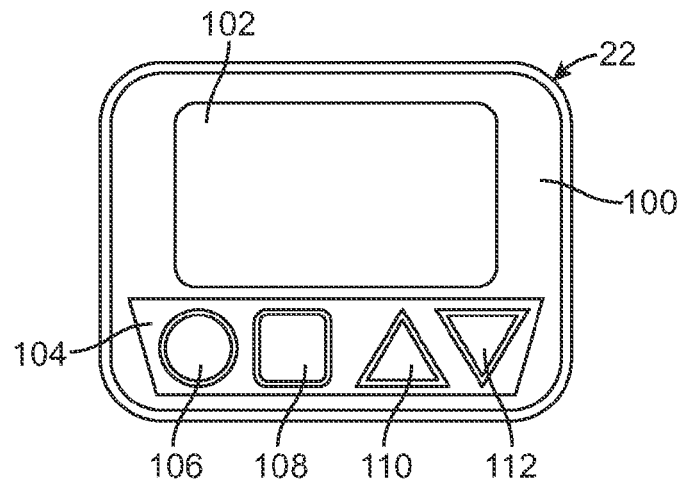
FIG. 4 is front view of a remote control (RC) used in the DBS system of FIG. 1.

Referring now to FIG. 4, one exemplary embodiment of an RC 20 will now be described. As previously discussed, the RC 20 is capable of communicating with the IPG 14, patient monitor 18, or CP 22. The RC 20 comprises a casing 100, which houses internal componentry (including a printed circuit board (PCB)), and a lighted display screen 102 and a button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. The button pad 104 includes a series of buttons 106, 108, 110, and 112, which allow the IPG 22 to be turned ON and OFF, provide for the adjustment or setting of stimulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 20 to switch between screen displays and/or parameters. The buttons 110 and 112 serve as up/down buttons that can actuated to increment or decrement any of stimulation parameters of the pulse generated by the IPG 14, including pulse amplitude, pulse width, and pulse rate. For example, the selection button 108 can be actuated to place the RC 16 in an "Pulse Amplitude Adjustment Mode," during which the pulse amplitude can be adjusted via the up/down buttons 110, 112, a "Pulse Width Adjustment Mode," during which the pulse width can be adjusted via the up/down buttons 110, 112, and a "Pulse Rate Adjustment Mode," during which the pulse rate can be adjusted via the up/down buttons 110, 112. Alternatively, dedicated up/down buttons can be provided for each stimulation parameter. Alternatively, rather than using up/down buttons, any other type of actuator, such as a dial, slider bar, or keypad, can be used to increment or decrement the stimulation parameters. Thus, it can be appreciated that any stimulation parameters programmed into the RC 20, and thus, the IPG 14, can be adjusted by the user via operation of the keypad 104. The RC 20 may have another button (not shown) that can be actuated to place the RC 20 either in a manual programming mode or an automatic programming mode, as previously discussed.

Figure 5:
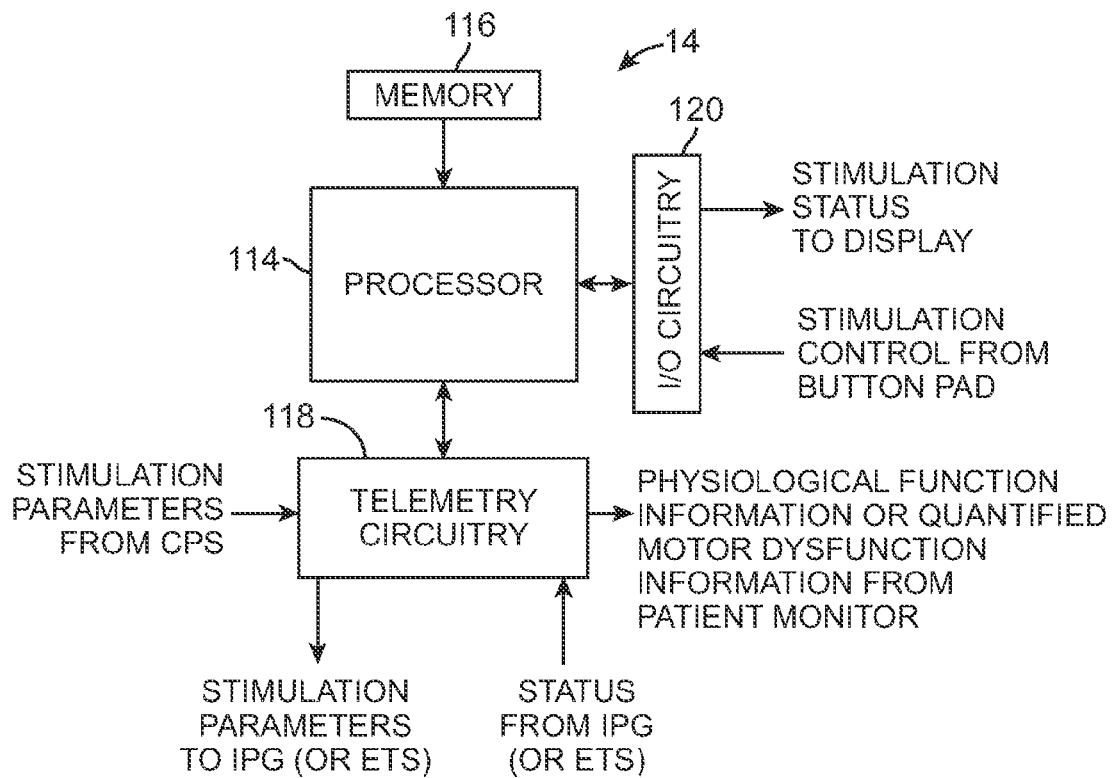
FIG. 5 is a block diagram of the internal components of the RC of FIG. 3.

Referring to FIG. 5, the internal components of an exemplary RC 20 will now be described. The RC 20 generally includes a processor 114 (e.g., a microcontroller), memory 116 that stores an operating program for execution by the processor 114, as well as stimulation parameters, input/output circuitry, and in particular, telemetry circuitry 118 for outputting stimulation parameters to the IPG 22 and receiving status information from the IPG 14, and input/output circuitry 120 for receiving stimulation control signals from the button pad 104 and transmitting status information to the display screen 102 (shown in FIG. 4). As well as controlling other functions of the RC 20, which will not be described herein for purposes of brevity, the processor 114 generates new stimulation parameters in response to the user operation of the button pad 104. These new stimulation parameters would then be transmitted to the IPG 14 via the telemetry circuitry 118, thereby adjusting the stimulation parameters stored in the IPG 14 and/or programming the IPG 14 with the stimulation parameters. The telemetry circuitry 118 can also be used to receive stimulation parameters from the CP 22 and/or physiological end-function information or quantified dysfunction information from the patient monitor 18. Further details of the functionality and internal componentry of the RC 20 are disclosed in U.S. Pat. No. 6,895,280, which has previously been incorporated herein by reference.

As briefly discussed above, modifying and programming the stimulation parameters in the programmable memory of the IPG 14 after implantation can also be performed by a physician or clinician using the CP 22, which can directly communicate with the IPG 14 or indirectly communicate with the IPG 14 via the RC 16. As shown in FIG. 1, the overall appearance of the CP 22 is that of a laptop personal computer (PC), and in fact, may be implemented using a PC that has been appropriately configured to perform the functions described herein. Thus, the programming methodologies can be performed by executing software instructions contained within the CP 22. Alternatively, such programming methodologies can be performed using firmware or hardware. In any event, the CP 22 determines the improved stimulation parameters based on the measured physiological end-functions or quantified dysfunction information and for subsequently programming the IPG 14 with the optimum or effective stimulation parameters.

Figure 6:
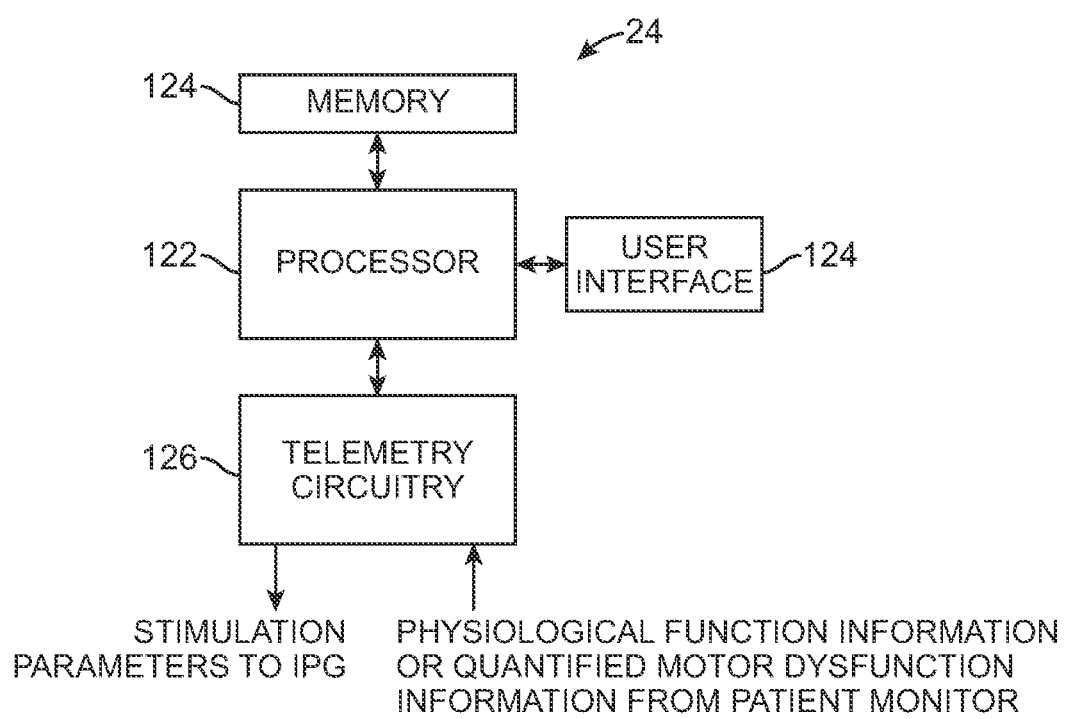
FIG. 6 is a block diagram of the internal components of a clinician's programmer (CP) used in the DBS system of FIG. 1.

To this end, the functional components of the CP 22 will now be described with reference to FIG. 6. The CP 22 generally includes a processor 122 (e.g., a central processor unit (CPU)), memory 124 for storing software that can be executed by the processor 122 to allow a clinician to selectively adjust stimulation parameters to be programmed into the IPG 14, and when the CP 22 is in the automated mode, automatically determining stimulation parameters to be programmed into the IPG 14 based on the measured physiological end-functions or quantified dysfunction information received from the patient monitor 18. The memory 124 also stores the estimated periods of time for the various symptoms of the dysfunction to resolve. The CP 22 further comprises a standard user interface 124 (e.g., a keyboard, mouse, joystick, display, etc.) to allow a clinician to input information and control the process), and telemetry circuitry 126 for receiving the physiological end-function information or quantified dysfunction information from the patient monitor 18, and outputting stimulation parameters to the IPG 14 for adjustment or programming of the stimulation parameters stored in the IPG 14. Further details discussing CPs are disclosed in U.S. Pat. No. 6,909,917, which is expressly incorporated herein by reference.

Figure 7:
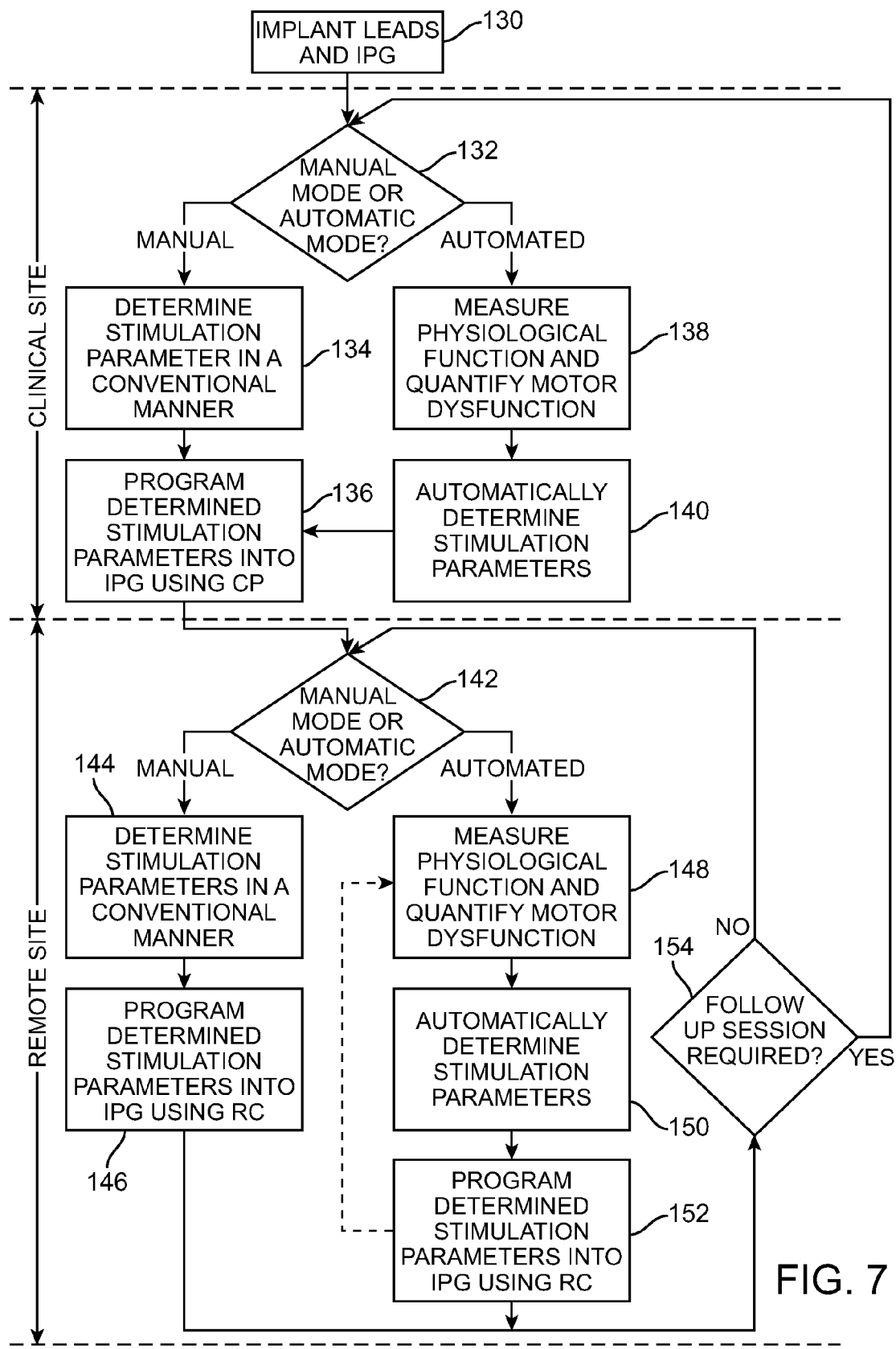
FIG. 7 is a flow diagram illustrating a method of operating the DBS system of FIG. 1.
Figure 8:
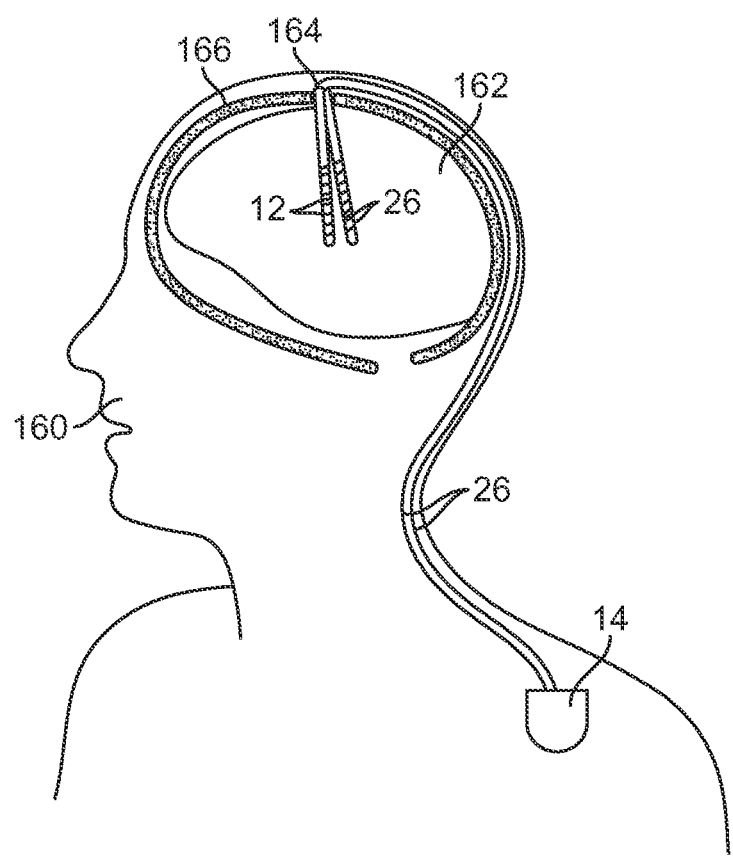
FIG. 8 is a cross-sectional view of a patient's head showing the implantation of stimulation leads and an IPG of the DBS system of FIG. 1.

Having described the structure and function of the DBS system 10, its operation will now be described with reference to FIG. 7. First, the stimulation leads 12, the extensions 24 and the IPG 14 are implanted within the patient (step 130). In particular, and with reference to FIG. 8, the stimulation leads 12 are introduced through a burr hole 164 formed in the cranium 166 of a patient 160, and introduced into the parenchyma of the brain 162 of a patient 160 in a conventional manner, such that the electrodes 26 are adjacent a target tissue region whose electrical activity is the source of the dysfunction (e.g., the ventrolateral thalamus, internal segment of globus pallidus, substantia nigra pars reticulate, subthalamic nucleus, or external segment of globus pallidus). Thus, stimulation energy can be conveyed from the electrodes 26 to the target tissue region to change the status of the dysfunction.

The IPG 14 may be generally implanted in a surgically-made pocket in the torso of the patient (e.g., the chest or shoulder region). The IPG 14 may, of course, also be implanted in other locations of the patient's body. The lead extensions 24, which may be subcutaneously advanced underneath the scalp of the patient to the IPG implantation site, facilitate locating the IPG 14 away from the exit point of the stimulation leads 12. In alternative embodiments, the IPG 14 may be directly implanted on or within the cranium 166 of the patient, as described in U.S. Pat. No. 6,920,359, which is expressly incorporated herein by reference. In this case, the lead extensions 24 may not be needed. After implantation, the IPG 14 is used to provide the therapeutic stimulation under control of the patient.

Next, the CP 22 is operated by the clinician to program stimulation parameters within the IPG 14 (steps 132-140). The CP 22 may be operated in either a manual mode or an automated mode (step 132) to program the stimulation parameters within the IPG 14. If the CP 22 is operated in the manual mode, the clinician determines the stimulation parameters to be programmed into the IPG 14 in a conventional manner (step 134), and then programs these stimulation parameters into the IPG 14 via the CP 22 (step 136). If the CP 22 is operated in the automated mode, the patient monitor 18 is operated to measure the physiological end-function indicating a change in the status of the dysfunction and optionally quantify the dysfunction based on the measured physiological end-function (step 138), and the CP 22 automatically determines the stimulation parameters (preferably, the optimum or most effective) based on the measured physiological end-function or quantified dysfunction (step 140). In one exemplary method, the CP 22 may be operated in the manual mode to utilize the expert judgment of the clinician as a starting point for determining the stimulation parameters, and then operated in the automated mode to fine-tune the stimulation parameters. The CP 22 may, e.g., automatically determine the stimulation parameters by using the heuristic or correlation approaches discussed above.

Significantly, the CP 22 is specifically designed to address the symptoms of dysfunctions that latently respond to electrical stimulation energy by waiting a predetermined period of time between adjustments of the stimulation parameters, as discussed above. In particular, and with reference to FIG. 9, the CP 22 initially selects one of a plurality of predetermined periods of time estimated for a plurality of symptoms to resolve in response to electrical stimulation therapy (step 200). This step can be accomplished with or without input from the physician or clinician. The CP 22 then evaluates the level of pre-stimulation symptoms of the patient (step 202), and generates a set of stimulation parameters based on this evaluation to minimize the symptoms and side effects of the electrical stimulation (step 204). The CP 22 then commands the IPG 14 to convey electrical stimulation energy to or from the relevant tissue region (by conveying electrical energy between selected electrodes 26 coupled to the corresponding electrical terminals 58) in accordance with generated set of stimulation parameters, thereby affecting the symptom to be suppressed (step 206). The CP 22 then waits the previously selected predetermined period of time estimated for the symptom to resolve in response to electrical stimulation therapy, thereby allowing the symptoms to "melt away" upon conveyance of the electrical energy (step 208), and then terminates the conveyance of the electrical stimulation energy (step 210). An optimization algorithm could optionally be used to find the best stimulation set based on one or more symptoms, noting the outcomes of the variety of stimulation parameters.

The CP 22 then evaluates the effect that the electrical stimulation energy has on the symptom or any side effects of the electrical stimulation energy based on information received from the patient monitor 18 (step 212). Alternatively, rather than obtaining information received from the patient monitor 18, subjective feedback can be provided by a human observer (e.g., user or clinician) and input into the CP 22. In either event, the CP 22 then determines if the symptom resolved in response to the first electrical stimulation energy (step 214). If the symptom resolves and the side effects of the electrical stimulation are minimal or non-existent, the CP 22 identifies the current stimulation parameter set as the stimulation parameter set to be programmed into the IPG 14 (step 216). If the symptom does not resolve or the side effects of the electrical stimulation is significant, the CP 22 again generates a set of stimulation parameters (different from the previously generated stimulation parameter set) (step 204), and again commands the IPG 14 to convey electrical stimulation energy to or from the tissue region (by conveying electrical energy between the selected electrodes 26 coupled to the corresponding electrical terminals 58) in accordance with the newly generated set of stimulation parameters (step 206), waits the previously selected predetermined period of time estimated for the symptom to resolve in response to electrical stimulation therapy (step 208), optionally terminates the conveyance of the electrical stimulation energy (e.g., if it is known that symptoms will not return when the conveyance of electrical stimulation energy is terminated) (step 210), and evaluates the effect that the electrical stimulation energy has on the symptom or any side effects of the electrical stimulation energy (step 212).

The CP 22 may define any stimulation parameter based on the evaluation or may simply use a predetermined set of stimulation parameters for the second stimulation parameter set. This process can be repeated as necessary until an optimum or effective set of stimulation parameter is determined and programmed into the IPG 14. The evaluation at step 212 may be the same for each iteration, so that the results at each point may be compared to determine the optimal stimulation parameter set. In a setting where a clinician or physician are not present, an alarm may be set off in the event that a problem occurs, the symptoms of the patient become intense, the side effects of the stimulation become intense, or the CP 22 otherwise encounters a situation where a physician or clinician should be present. For purposes of safety, the CP 22 may also limit the total electrical charge injected into the patient. The CP 22 may also limit the electrodes 26 used to provide the electrical stimulation. For example, if the physician or clinician knows that the most distal electrode in an area should be note used to stimulate, the physician or clinician may instruct the CP 22 not to stimulate using this electrode.

Referring back to FIG. 8, the CP 22 programs the stimulation parameter set or sets into the IPG 14 without or without the aid of the clinician (i.e., by either automatically programming the IPG 14 with the stimulation parameters or suggesting stimulation parameters to the clinician who can then prompt the RC 14 to program the suggested stimulation parameters into the IPG (step 136).

Once the DBS system 10 is properly fitted to the patient, the stimulation parameters programmed into the IPG 14 may be adjusted at a remote site outside of the clinical setting (steps 142-154). In particular, the RC 20 may optionally be operated between a manual mode and an automated mode (assuming that the patient monitor 18 is ambulatory or otherwise cost efficient to maintain within the patient's home) in a similar manner as the CP 22 (step 142). Notably, it may be necessary to limit the range of effects that could take place during the automated may, which may otherwise require the judgment or intervention of a clinician to oversee full automated operation of the process. If the RC 20 is operated in the manual mode, the patient may determine the stimulation parameters to be programmed into the IPG 14 in a conventional manner (typically, simply by using the RC 20 to adjust the stimulation parameters already programmed into the IPG 14) (step 144), and then may reprogram the adjusted stimulation parameters into the IPG 14 via the RC 20 (step 146). If the RC 20 is operated in the automated mode, the patient monitor 18 is operated to measure the physiological end-function indicating a change in the status of the dysfunction and optionally quantify the dysfunction based on the measured physiological end-function (step 148), the RC 20 automatically determines the stimulation parameters (preferably, the optimum or most effective) based on the measured physiological end-function or quantified dysfunction (step 150), and programs these stimulation parameters into the IPG 14 without or without patient intervention (step 152). Operation of the RC 20 in the automated mode and can be performed continuously (by iteratively performing steps 148-152) to compensate for changes in the dysfunction as a result of disease progression, motor re-learning, etc. If a follow-up programming session is necessary (step 154), steps 132-140 can be repeated.

It should be noted that, while the DBS system 10 and method of using the same has been described in the contact of programming an IPG or other implantable device, an external device, such as an external trial stimulation (ETS) (not shown) may be programmed in the same manner. The major difference between an ETS and the IPG 14 is that the ETS is a non-implantable device that is used on a trial basis after the stimulation leads 12 have been implanted and prior to implantation of the IPG 14, to test the responsiveness of the stimulation that is to be provided. Further details of an exemplary ETS are described in U.S. Pat. No. 6,895,280, which is expressly incorporated herein by reference.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neurostimulation system for use with a patient suffering from a symptom of a disease that latently responds to electrical stimulation therapy, comprising:
at least one electrical terminal to which at least one electrode can be coupled;
output stimulation circuitry coupled to the at least one electrical terminal;
memory storing a plurality of predetermined periods of time estimated for a plurality of symptoms to resolve in response to electrical stimulation therapy; and
control circuitry configured for allowing selection of one of the predetermined periods of time, controlling the output stimulation circuitry to convey first electrical stimulation energy to or from the at least one electrical terminal in accordance with a first set of stimulation parameters, waiting the selected predetermined period of time, and conveying second electrical stimulation energy to or from the tissue region in accordance with a second set of stimulation parameters different from the first set of stimulation parameters.

2. The neurostimulation system of claim 1, further comprising processing circuitry configured for evaluating the effect that the first electrical stimulation energy has on the symptom after waiting selected predetermined period of time.

3. The neurostimulation system of claim 2, wherein the processing circuitry is further configured for defining the second set of stimulation parameters based on the evaluation.

4. The neurostimulation system of claim 2, wherein the processing circuitry is further configured for determining that the symptom did not resolve in response to the first electrical stimulation energy after waiting the selected predetermined period of time, wherein the second electrical stimulation energy is conveyed in response to the determination that the symptom did not resolve.

5. The neurostimulation system of claim 1, wherein at least one of the predetermined periods of time is equal to or greater than five seconds.

6. The neurostimulation system of claim 1, wherein at least one of the predetermined periods of time is equal to or greater than one minute.

7. The neurostimulation system of claim 1, wherein at least one of the predetermined periods of time is equal to or greater than five minutes.

8. The neurostimulation system of claim 1, wherein at least one of the predetermined periods of time is equal to or greater than one hour.

9. The neurostimulation system of claim 1, wherein the control circuitry is configured for terminating conveyance of the first electrical stimulation energy only after waiting the selected predetermined period of time.

10. A method of providing therapy to a patient suffering from a symptom of a disease that latently responds to electrical neurostimulation therapy, comprising: conveying first electrical neurostimulation energy to or from a tissue region of the patient in accordance with a first set of stimulation parameters, thereby affecting the symptom; waiting a predetermined period of time estimated for the symptom to resolve in response to electrical neurostimulation therapy; and conveying second electrical neurostimulation energy to or from the tissue region in accordance with a second set of stimulation parameters different from the first set of stimulation parameters.

11. The method of claim 10, further comprising evaluating the effect that the first electrical neurostimulation energy has on the symptom after waiting the predetermined period of time.

12. The method of claim 11, further comprising defining the second set of stimulation parameters based on the evaluation.

13. The method of claim 11, further comprising determining that the symptom did not resolve in response to the first electrical neurostimulation energy after waiting the predetermined period of time, wherein the second electrical neurostimulation energy is conveyed in response to the determination that the symptom did not resolve.

14. The method of claim 10, wherein the disease is a neurological disorder.

15. The method of claim 14, wherein the neurological disorder is Parkinson's disease.

16. The method of claim 10, wherein the predetermined period of time is equal to or greater than five seconds.

17. The method of claim 10, wherein the predetermined period of time is equal to or greater than one minute.

18. The method of claim 10, wherein the predetermined period of time is equal to or greater than five minutes.

19. The method of claim 10, wherein the predetermined period of time is equal to or greater than one hour.

20. The method of claim 10, further comprising programming the second set of stimulation parameters into the memory of a neurostimulation device.

21. The method of claim 10, further comprising selecting one of a plurality of predetermined periods of time estimated for a plurality of symptoms to resolve in response to electrical neurostimulation therapy, wherein the selected predetermined period of time is the waited predetermined period of time.

22. The method of claim 10, wherein the conveyance of the first electrical neurostimulation energy is terminated only after waiting the predetermined period of time.

* * * * *